United States Patent
Guerra et al.

(10) Patent No.: US 11,326,007 B2
(45) Date of Patent: May 10, 2022

(54) BRANCHED PERFLUOROVINYL ETHER COMPOUNDS, METHODS OF MAKING THE SAME, AND FLUOROPOLYMERS DERIVED FROM THE BRANCHED PERFLUOROVINYL ETHER COMPOUNDS

(71) Applicant: 3M INNOVATIVE PROPERTIES COMPANY, St. Paul, MN (US)

(72) Inventors: Miguel A. Guerra, Woodbury, MN (US); Michael G. Costello, Afton, MN (US); Tatsuo Fukushi, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 17/267,853

(22) PCT Filed: Aug. 27, 2019

(86) PCT No.: PCT/IB2019/057206
§ 371 (c)(1),
(2) Date: Feb. 11, 2021

(87) PCT Pub. No.: WO2020/044232
PCT Pub. Date: Mar. 5, 2020

(65) Prior Publication Data
US 2021/0171680 A1    Jun. 10, 2021

Related U.S. Application Data

(60) Provisional application No. 62/724,666, filed on Aug. 30, 2018.

(51) Int. Cl.
| | |
|---|---|
| C08F 214/18 | (2006.01) |
| C08F 214/22 | (2006.01) |
| C08F 16/24 | (2006.01) |
| C08F 114/18 | (2006.01) |
| C08F 214/26 | (2006.01) |
| C08F 214/28 | (2006.01) |
| C08F 214/24 | (2006.01) |
| C08F 14/18 | (2006.01) |
| C08F 214/20 | (2006.01) |
| C07C 41/18 | (2006.01) |
| C07C 43/17 | (2006.01) |
| C07C 51/58 | (2006.01) |
| C07C 55/40 | (2006.01) |
| C08F 216/14 | (2006.01) |

(52) U.S. Cl.
CPC ........ *C08F 214/222* (2013.01); *C08F 14/185* (2013.01); *C08F 16/24* (2013.01); *C08F 114/185* (2013.01); *C08F 214/202* (2013.01); *C08F 214/242* (2013.01); *C08F 214/262* (2013.01); *C08F 214/282* (2013.01); *C07C 41/18* (2013.01); *C07C 43/17* (2013.01); *C07C 51/58* (2013.01); *C07C 55/40* (2013.01); *C08F 216/1408* (2013.01)

(58) Field of Classification Search
CPC .................. C08F 214/222; C08F 16/24; C08F 216/1408; C08F 214/184; C08F 214/242; C08F 214/262; C08F 214/282; C08F 114/185; C08F 14/185
See application file for complete search history.

(56) References Cited

U.S. PATENT DOCUMENTS

| | | | |
|---|---|---|---|
| 3,250,808 A | 5/1966 | Moore, Jr. | |
| 3,274,239 A | 9/1966 | Selman | |
| 4,035,565 A | 7/1977 | Apotheker | |
| 4,542,238 A | 9/1985 | Ishikawa | |
| 7,671,112 B2 | 3/2010 | Hintzer | |
| 2007/0015937 A1 | 1/2007 | Hintzer | |
| 2010/0113691 A1* | 5/2010 | Peng | C08F 14/18 524/845 |
| 2013/0046058 A1* | 2/2013 | Pham | C08F 8/22 525/55 |
| 2013/0303710 A1* | 11/2013 | Brothers | C08F 8/06 525/387 |

FOREIGN PATENT DOCUMENTS

| | | |
|---|---|---|
| CN | 103936905 | 7/2014 |
| EP | 1 947 163 | 7/2008 |
| WO | WO 2018-034838 | 2/2018 |

OTHER PUBLICATIONS

ASTM D 2196-05, "Standard Test Methods for Rheological Properties of Non-Newtonian Materials by Rotational Viscometer," 5 pages.

Fenichev, "Catalytic Synthesis of Certain Perfluorinated Ketones and Study of Their Structure by 19F NMR Spectroscopy," Russian Journal of Applied Chemistry, Jun. 2013, vol. 86, No. 8, pp. 1243-1251.

International Search Report for PCT International Application No. PCT/IB2019/057206, dated Jan. 14, 2020, 4 pages.

* cited by examiner

*Primary Examiner* — Ling Siu Choi
*Assistant Examiner* — David L Miller
(74) *Attorney, Agent, or Firm* — Julie Lapos-Kuchar

(57) ABSTRACT

Described herein is method of making branched perfluorinated compounds, specifically $(CF_3)_2CFCF(CF_3)OCF(CF_3)C(=O)F$ and $(CF_3)_2CFCF(CF_3)OCF=CF_2$. Also disclosed herein is a fluoropolymer derived from the branched perfluorovinyl ether monomer and methods of making the fluoropolymer.

9 Claims, No Drawings

BRANCHED PERFLUOROVINYL ETHER COMPOUNDS, METHODS OF MAKING THE SAME, AND FLUOROPOLYMERS DERIVED FROM THE BRANCHED PERFLUOROVINYL ETHER COMPOUNDS

CROSS REFERENCE TO RELATED APPLICATIONS

This application is a national stage filing under 35 U.S.C. 371 of PCT/IB2019/057206, filed Aug. 27, 2019, which claims the benefit of U.S. Application No. 62/724,666, filed Aug. 30, 2018, the disclosure of which is incorporated by reference in its/their entirety herein.

TECHNICAL FIELD

A branched perfluorovinyl ether compound is disclosed along with a method of making such compounds. Also disclosed is a fluoropolymer derived from the branched perfluorovinyl ether compound and articles therefrom.

SUMMARY

There is a desire to identify novel monomers which provide new fluoropolymers having improved properties, such as a reduced viscosity.

In one aspect, a method of making a compound is disclosed. The method comprising: contacting $(CF_3)_2CF-C(=O)-CF_3$ with hexafluoropropylene oxide in the presence of a metal fluoride catalyst and an aprotic solvent to form an acid fluoride of $(CF_3)_2CFCF(CF_3)OCF(CF_3)C(=O)F$.

In one embodiment, the method further comprises decarboxylating $(CF_3)_2CFCF(CF_3)OCF(CF_3)C(=O)F$ to form a vinyl ether of $(CF_3)_2CFCF(CF_3)OCF=CF_2$.

In another aspect, the monomer, $(CF_3)_2CFCF(CF_3)OCF=CF_2$ is disclosed.

In yet another aspect, a fluoropolymer is disclosed, wherein the fluoropolymer is derived from $(CF_3)_2CFCF(CF_3)OCF=CF_2$.

In still another aspect, a method of making a fluoropolymer is disclosed. The method comprising reacting $(CF_3)_2CFCF(CF_3)OCF=CF_2$ with a free radical initiator.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term

"a", "an", and "the" are used interchangeably and mean one or more; and

"and/or" is used to indicate one or both stated cases may occur, for example A and/or B includes, (A and B) and (A or B);

"backbone" refers to the main continuous chain of the polymer, excluding the sites of polymer initiation and termination;

"interpolymerized" refers to monomers that are polymerized together to form a polymer backbone;

"monomer" is a molecule which can undergo polymerization which then forms part of the essential structure of a polymer;

"perfluorinated" means a group or a compound derived from a hydrocarbon wherein all hydrogen atoms have been replaced by fluorine atoms. A perfluorinated compound may however still contain other atoms than fluorine and carbon atoms, like oxygen atoms, chlorine atoms, bromine atoms and iodine atoms; and "polymer" refers to a macrostructure having a number average molecular weight (Mn) of at least 10,000 daltons, at least 20,000 daltons, at least 30,000 daltons, at least 40,000 daltons, at least 50,000 dalton, at least 100,000 dalton, at least 300,000 dalton, at least 500,000 dalton, at least, 750,000 dalton, at least 1,000,000 dalton, or even at least 1,500,000 dalton and not such a high molecular weight as to cause premature gelling of the polymer.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

As used herein, "comprises at least one of" A, B, and C refers to element A by itself, element B by itself, element C by itself, A and B, A and C, B and C, and a combination of all three.

Disclosed herein is a method for making branched perfluorinated compounds, a novel branched perfluorovinyl ether compound, and fluoropolymers derived therefrom.

Method of Making Branched Perfluorinated Compounds

A branched perfluorinated ether acid fluoride compound of the formula $(CF_3)_2CFCF(CF_3)OCF(CF_3)C(=O)F$ is made by contacting a perfluorinated ketone of formula $(CF_3)_2CF-C(=O)-CF_3$ with hexafluoropropylene oxide in the presence of a metal fluoride catalyst and an aprotic solvent.

The perfluorinated ketone, $(CF_3)_2CF-C(=O)-CF_3$, is commercially available under the trade designation "3M NOVEC 5110 INSULATING GAS" from 3M Co., Maplewood, Minn., or can be synthesized using techniques known in the art, for example reaction of hexafluoropropylene with trifluoroacetyl fluoride in KF and diglyme.

Hexafluoropropylene oxide (HFPO) can be obtained from specialty chemical companies.

Typically, the mole ratio of $(CF_3)_2CF-C(=O)-CF_3$ with HFPO is at least 1:2 to at most 2:1 or even at least 1:1.5 to at most 1.5:1. A ratio of about 1:1 ratio is preferable, if the reaction proceeds ideally with minimal side-reactions, such a side-reaction can include two HFPO molecules reacting with one perfluorinated ketone compound.

Metal fluoride catalysts are known in the art. Exemplary metal fluoride catalysts include: CsF, KF, $AlF_3$, and combinations thereof. Because the metal fluoride catalyst is regenerated during the reaction, typically low amount (e.g., less than 20, 15, 10, 5, 2, or even 1 mole % of the metal fluoride catalyst versus the moles of $(CF_3)_2CF-C(=O)-CF_3$) are used.

A solvent may be used to solubilize the reactants for a reaction to occur. Useful solvents include organic solvents, such as aprotic solvents. Aprotic solvents include, ethers (such as bis(2-methoxyethyl) ether and tetraethylene glycol dimethyl ether), nitriles (such as acetonitirile, adiponitrile, and benzonitrile), dime thylsulfoxide, N-methylpyrrolidinone (NMP), N,N-dimethylformamide (DMF), and tetrahydrothiophene-1,1-dioxide (sulfolane), which can be used individually or as a mixture.

In one embodiment, HFPO and the perfluorinated ketone are combined in a reactor that initially is evacuated. Thus, during the reaction of HFPO with the perfluorinated ketone, the reactor may initially start below atmospheric and increase up to ambient and or higher pressures (e.g., up to 30 psi or 206 kilopascals). In one embodiment of the present disclosure, the reaction between $(CF_3)_2CFC(=O)CF_3$ and HFPO may be conducted at a temperature of at least −20, −10, −5, 0, 5 10, 20, or even 25° C. and at most 30, 40 or even 50° C. Typically, the reaction occurs in less than about 2 hours, 4 hours, or even 8 hours; and at most about 4 hours, 6 hours, 8 hours, 10 hours, or even 24 hours.

In one embodiment, the reaction according to the present disclosure can generate the desired perfluorinated ether acid fluoride with a conversion from the corresponding ketone of at least 50, 60, 70, 80, 85 or even 90% by mole. If improved selectivity for forming $(CF_3)_2CFCF(CF_3)OCF(CF_3)C(=O)F$ is desired, the reaction can run at a low temperature (e.g., less than 0° C.), however longer reactions times (e.g., more than 1 day) may be necessary to achieve sufficient conversion.

Unexpectedly, as shown in the Example Section below, the coupling reaction described above appears to be selective for $(CF_3)_2CFCOCF_3$, as opposed to $(CF_3)_2CFCOCF_2CF_3$, which comprises just one additional $—CF_2—$ group. Although not wanting to be limited by theory, it is believed that steric hindrance may be responsible for the low product yield in Comparative Example A.

The resulting branched perfluoroether acid fluoride compound, $(CF_3)_2CFCF(CF_3)OCF(CF_3)C(=O)F$, can be purified before subsequent use, which is especially important when subsequently used in polymerization reactions. Purification can be done by conventional means including distillation, absorption, extraction, and chromatography. Purification can be done to isolate $(CF_3)_2CFCF(CF_3)OCF(CF_3)C(=O)F$ from impurities, such as starting materials, byproducts, etc. The term "purified form" as used herein means the compound is at least 75, 80, 85, 90, 95, 98, or even 99 wt % pure.

The $(CF_3)_2CFCF(CF_3)OCF(CF_3)C(=O)F$ may be decarboxylated to form the vinyl ether, $(CF_3)_2CFCF(CF_3)OCF=CF_2$. Such decarboxylation techniques are known in the art. For example, the perfluorinated ether acid fluoride may be neutralized (e.g., with sodium carbonate) to form the corresponding acid salt, which upon heating (e.g., temperatures of at least 100, 150, or even 175° C. and at most 250, 300, or even 350° C.) can decarboxylate to form the corresponding vinyl ether, $(CF_3)_2CFCF(CF_3)OCF=CF_2$.

The $(CF_3)_2CFCF(CF_3)OCF=CF_2$ may be isolated by known methods. For example, the crude product is washed with water, neutralizing any outstanding acid (e.g., addition of sodium bicarbonate) and rewashing the product, generating a phase split and the lower (fluorochemical) phase is collected to obtain $(CF_3)_2CFCF(CF_3)OCF=CF_2$.

In some embodiments, further purification of the crude product is sometimes not necessary. The elimination of the purification step may reduce processing time and cost. If desired, the reaction mixture or crude product may be purified, for example, by column fractionation to generate a purified form of $(CF_3)_2CFCF(CF_3)OCF=CF_2$.

The monomer compound, $(CF_3)_2CFCF(CF_3)OCF=CF_2$, disclosed herein can be used in the polymerization of monomers to form a polymer with a reduced viscosity Fluoropolymer Compositions $(CF_3)_2CFCF(CF_3)OCF=CF_2$ disclosed above can be polymerized in the presence of an initiator to yield a fluoropolymer.

In one embodiment, $(CF_3)_2CFCF(CF_3)OCF=CF_2$ can be polymerized with a polymerizable fluorinated olefinic monomer, wherein the polymerizable fluorinated olefinic monomer is different from $(CF_3)_2CFCF(CF_3)OCF=CF_2$.

The polymerizable fluorinated olefinic monomers are not particularly limited so long as they have free radical polymerizability. These polymerizable fluorinated olefinic monomers may be perfluorinated or partially fluorinated monomers. Such olefins, typically contain from 2 to 20 carbon atoms. In addition to fluorine atoms and, as the case may be, hydrogen atoms, the olefins may also contain Cl atoms and/or oxygen ether atoms.

The curable fluoropolymer is derived from a fluorinated monomer. Exemplary fluorinated monomers include: tetrafluoroethylene (TFE), hexafluoropropylene (HFP), trifluorochloroethylene (CTFE), vinylidene fluoride (VDF), vinyl fluoride (VF), trifluoroethylene, 3,3,3-trifluoropropene-1, pentafluoropropene (e.g., 2-hydropentafluoropropylene and 1-hydrofluoropropylene), 2,3,3,3-tetrafluoropropene, perfluorovinyl ethers (including perfluoroallyl vinyl ethers and perfluoroalkoxy vinyl ethers), perfluoroallyl ethers (including perfluoroalkyl allyl ethers and perfluoroalkoxy allyl ethers), perfluoroalkyl vinyl monomers, and combinations thereof.

Suitable perfluoroalkyl vinyl monomers correspond to the general formula: $CF_2=CF—R^d{}_f$ or $CH_2=CH—R^d{}_f$ wherein $R^d{}_f$ represents a perfluoroalkyl group of 1-10, or even 1-5 carbon atoms.

Examples of perfluorovinyl ethers that can be used in the present disclosure include those that correspond to the formula: $CF_2=CF—O—R_f$ wherein $R_f$ represents a perfluorinated aliphatic group that may contain no, one or more oxygen atoms and up to 12, 10, 8, 6 or even 4 carbon atoms. Exemplary perfluorinated vinyl ethers correspond to the formula: $CF_2=CFO(R^a{}_fO)_n(R^b{}_fO)_mR^c{}_f$ wherein $R^a{}_f$ and $R^b{}_f$ are different linear or branched perfluoroalkylene groups of 1-6 carbon atoms, in particular 2-6 carbon atoms, m and n are independently 0-10 and $R^c{}_f$ is a perfluoroalkyl group of 1-6 carbon atoms. Specific examples of perfluorinated vinyl ethers include: perfluoro (methyl vinyl) ether (PMVE), perfluoro (ethyl vinyl) ether (PEVE), perfluoro (n-propyl vinyl) ether (PPVE-1), perfluoro-2-propoxypropylvinyl ether (PPVE-2), perfluoro-3-methoxy-n-propylvinyl ether, perfluoro-2-methoxy-ethylvinyl ether, $CF_3—(CF_2)_2—O—CF(CF_3)—CF_2—O—CF(CF_3)—CF_2—O—CF=CF_2$, and perfluoro-methoxy-methylvinylether $(CF_3—O—CF_2—O—CF=CF_2)$, and mixtures thereof.

Examples of perfluoroallyl ethers that can be used in the present disclosure include those that correspond to the formula: $CF_2=CF(CF_2)—O—R_f$ wherein $R_f$ represents a perfluorinated aliphatic group that may contain no, one or more oxygen atoms and up to 10, 8, 6 or even 4 carbon atoms. Specific examples of perfluorinated allyl ethers include: $CF_2=CF_2—CF_2—O—(CF_2)_nF$ wherein n is an integer from 1 to 5, and
$CF_2=CF_2—CF_2—O—(CF_2)_n—O—(CF_2)_y—F$ wherein x is an integer from 2 to 5 and y is an integer from 1 to 5. Specific examples of perfluorinated allyl ethers include: perfluoro (methyl allyl) ether $(CF_2=CF—CF_2—O—CF_3)$, perfluoro (ethyl allyl) ether, perfluoro (n-propyl allyl) ether, perfluoro-2-propoxypropyl allyl ether, perfluoro-3-methoxy-n-propylallyl ether, perfluoro-2-methoxy-ethyl allyl ether, perfluoro-methoxy-methyl allyl ether, and $CF_3—(CF_2)_2—O—CF(CF_3)—CF_2—O—CF(CF_3)—CF_2—O—CF_2CF=CF_2$, and mixtures thereof.

In addition to these polymerizable fluorinated olefinic monomers, the fluoropolymers may contain units derived from non-fluorinated olefinic monomers. Such non-fluorinated olefinic monomers, typically contain from 2 to 20 carbon atoms and may also contain Cl atoms and/or oxygen ether atoms. Exemplary non-fluorinated olefinic monomers include propylene (P) and ethylene (E), vinyl chloride, vinylidene chloride, and combinations thereof.

In one embodiment, the fluoropolymer is derived from vinylidene fluoride, a perfluorinated vinyl ether (such as PMVE), and $(CF_3)_2CFCF(CF_3)OCF=CF_2$.

In one embodiment, the fluoropolymer is not derived from tetrafluoroethylene.

In one embodiment, the fluoropolymer is not derived from vinylidene fluoride, vinyl fluoride, or a hydrocarbon monomer (such as ethylene or propylene).

In one embodiment, the mole ratio of $(CF_3)_2CFCF(CF_3)OCF=CF_2$ to the total moles of other monomer used to make the fluoropolymer is 95:5 to 5:95.

In one embodiment, the fluoropolymer is derived from less than 5, 2, or even 1 mole % of $(CF_3)_2CFCF(CF_3)OCF=CF_2$ as on the total moles of monomer used in the fluoropolymer.

In one embodiment, the fluoropolymer is derived from at least 5, 10, 20, or even 30 mole % $(CF_3)_2CFCF(CF_3)OCF=CF_2$ and at most 40, 50, or even 60 mole % of $(CF_3)_2CFCF(CF_3)OCF=CF_2$ as on the total moles of monomer used in the fluoropolymer.

In another embodiment, the fluoropolymer is derived from at least 40, 50, 60, or even 65 mole % $(CF_3)_2CFCF(CF_3)OCF=CF_2$ and at most 80, 90, or even 95 mole % of $(CF_3)_2CFCF(CF_3)OCF=CF_2$ as on the total moles of monomer used in the fluoropolymer.

In one embodiment, the fluoropolymer of the present disclosure comprises an interpolymerized monomeric unit of

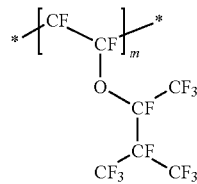

where * is a site of chain propagation along the polymer backbone and "m" is the average number of times that monomer unit appears along the polymer backbone. Typically, the interpolymerized monomeric unit shown above is randomly polymerized throughout the polymer backbone and thus, two or more of these segments may, or may not, be adjacent to one another. In one embodiment, the m is an integer of at least 1, 2, 3, 4, 6, or even 10; and at most 20, 50, 100, or even 500.

The fluoropolymers of the present disclosure can be obtained with any of the known polymerization techniques, however, the fluoropolymers are preferably made through an aqueous emulsion polymerization process, which can be conducted in a known manner including batch, semi-batch, or continuous polymerization techniques. The reactor vessel for use in the aqueous emulsion polymerization process is typically a pressurizable vessel capable of withstanding the internal pressures during the polymerization reaction. Typically, the reaction vessel will include a mechanical agitator, which will produce thorough mixing of the reactor contents and heat exchange system. Any quantity of the monomer(s) may be charged to the reactor vessel. The monomers may be charged batchwise or in a continuous or semi-continuous manner. By semi-continuous it is meant that a plurality of batches of the monomer are charged to the vessel during the course of the polymerization. The independent rate at which the monomers are added to the kettle will depend on the consumption rate of the particular monomer with time. Preferably, the rate of addition of monomer will equal the rate of consumption of monomer, i.e. conversion of monomer into polymer.

The reaction kettle is charged with water, the amounts of which are not critical. To the aqueous phase there is generally also added a fluorinated surfactant, typically a non-telogenic fluorinated surfactant, although aqueous emulsion polymerization without the addition of fluorinated surfactant may also be practiced. When used, the fluorinated surfactant is typically used in amount of 0.01% by weight to 1% by weight. Suitable fluorinated surfactants include any fluorinated surfactant commonly employed in aqueous emulsion polymerization. In one embodiment, the fluorinated surfactants are of the general formula:

$$[R_f\text{—O-L-COO}^-]_i X_i^+$$

wherein L represents a linear partially or fully fluorinated alkylene group or an aliphatic hydrocarbon group, $R_f$ represents a linear partially or fully fluorinated aliphatic group or a linear partially or fully fluorinated group interrupted with one or more oxygen atoms, $X_i^+$ represents a cation having the valence i and i is 1, 2 and 3. Specific examples are described in, for example, US Pat. Publ. 2007/0015937 (Hintzer et al.). Exemplary emulsifiers include: $CF_3CF_2OCF_2CF_2OCF_2COOH$, $CHF_2(CF_2)_5COOH$, $CF_3(CF_2)_6COOH$, $CF_3O(CF_2)_3OCF(CF_3)COOH$, $CF_3CF_2CH_2OCF_2CH_2OCF_2COOH$, $CF_3O(CF_2)_3OCHFCF_2COOH$, $CF_3O(CF_2)_3OCF_2COOH$, $CF_3(CF_2)_3(CH_2CF_2)_2CF_2CF_2COOH$, $CF_3(CF_2)_2CH_2(CF_2)_2COOH$, $CF_3(CF_2)_2COOH$, $CF_3(CF_2)_2(OCF(CF_3)CF_2)OCF(CF_3)COOH$, $CF_3(CF_2)_2(OCF_2CF_2)_4OCF(CF_3)COOH$, $CF_3CF_2O(CF_2CF_2O)_3CF_2COOH$, and their salts. In one embodiment, the molecular weight of the surfactant is less than 1500, 1000, or even 500 grams/mole.

These fluorinated surfactants may be used alone or in combination as a mixture of two or more of them. The amount of the surfactant is well below the critical micelle concentration, generally within a range of from 250 to 5,000 ppm (parts per million), preferably 250 to 2000 ppm, more preferably 300 to 1000 ppm, based on the mass of water to be used.

The polymerization is usually initiated after an initial charge of monomer by adding an initiator or initiator system to the aqueous phase. For example, peroxides can be used as free radical initiators. Specific examples of peroxide initiators include, hydrogen peroxide, diacylperoxides such as diacetylperoxide, dipropionylperoxide, dibutyrylperoxide, dibenzoylperoxide, benzoylacetylperoxide, diglutaric acid peroxide and dilaurylperoxide, and further water soluble per-acids and water-soluble salts thereof such as e.g. ammonium, sodium or potassium salts. Examples of per-acids include peracetic acid. Esters of the peracid can be used as well and examples thereof include tert-butylperoxyacetate and tert-butylperoxypivalate. A further class of initiators that can be used are water soluble azo-compounds. Suitable redox systems for use as initiators include for example a combination of peroxodisulphate and hydrogen sulphite or disulphite, a combination of thiosulphate and peroxodisulphate or a combination of peroxodisulphate and hydrazine. Further initiators that can be used are ammonium-alkali- or earth alkali salts of persulfates, permanganic or manganic acid or manganic acids. The amount of initiator employed is typically between 0.03 and 2% by weight, preferably between 0.05 and 10% by weight based on the total weight of the polymerization mixture. The full amount of initiator may be added at the start of the polymerization or the initiator can be added to the polymerization in a continuous way during the polymerization. One can also add part of the initiator at the start and the remainder in one or separate additional portions during the polymerization. Accelerators such as for example water-soluble salts of iron, copper and silver may preferably also be added.

During the initiation of the polymerization reaction, the sealed reactor kettle and its contents are conveniently preheated to the reaction temperature. Polymerization temperatures are from 20° C. to 150° C., preferred from 30° C. to 110° C. and most preferred from 40° C. to 100° C. The polymerization pressure is typically between 4 and 30 bar, in particular 8 to 20 bar. The aqueous emulsion polymerization system may further comprise auxiliaries, such as buffers and complex-formers.

The amount of polymer solids that can be obtained at the end of the polymerization is typically between 10% and 45% by weight, preferably between 20% and 40% by weight and the average particle size of the resulting fluoropolymer in an aqueous emulsion is typically at least 50, 60, 70, or even 80 nm and at most 100, 200, 300, 400, or even 500 nm (nanometers).

In one embodiment, the fluoropolymers of the present disclosure are perfluorinated. In other words, all of the C—H bonds in the polymer backbone are replaced by C—F bonds, although the end groups may or may not be fluorinated. In one embodiment, the fluoropolymers of the present disclosure are highly fluorinated, meaning that 80%, 90%, 95%, or even 99% of the C—H bonds in the polymer backbone are replaced by C—F bonds. In another embodiment, the fluoropolymers of the present disclosure are partially fluorinated, meaning the polymer backbone (excluding the end groups) comprises at least one C—H bond and one C—F bond.

The resulting fluoropolymers of the present disclosure may be amorphous (i.e., having no distinct melting point) or may be crystalline in nature.

In one embodiment, the polymers disclosed herein have a reduced viscosity, for example, having a viscosity of less than 10000, 8000, or even 6000 poise as measured by a Brookfield viscometer in accordance with ASTM D 2196-05.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

The following abbreviations are used in this section: mL=milliliters, g=grams, lb=pounds, min=minutes, h=hours, NMR=nuclear magnetic resonance, eq=equivalent, mmHg=millimeters mercury, ° C.=degrees Celsius, ° F.=degrees Farenheit, phr=parts per hundred rubber, MPa=mega Pascal, psi=pounds per square inch, Abbreviations for materials used in this section, as well as descriptions of the materials, are provided in Table 1.

TABLE 1

Materials List

| DESIGNATION | DESCRIPTION | SOURCE |
|---|---|---|
| Spray dried KF | Spray dried potassium fluoride | Sigma-Aldrich, St. Louis, MO |
| $(CF_3)_2CFCOCF_3$ | C5 ketone obtained under the trade designation "3M NOVEC 5110 INSULATING GAS" | 3M Co., Maplewood, MN |
| $(CF_3)_2CFCOCF_2CF_3$ | C6 ketone available under the trade designation "3M NOVEC 1230 FIRE PROTECTION FLUID" | 3M Co. |
| Tetraglyme | $CH_3O(C_2H_4O)_4CH_3$ | Sigma-Aldrich |
| $Na_2CO_3$ | Sodium carbonate | Sigma-Aldrich |
| Glyme | $CH_3OCH_2CH_2OCH_3$ | Sigma-Aldrich |
| Emulsifier | $CF_3$—O—$(CF_2)_3$—O—CFH—$CF_2$—$COONH_4$ | Prepared as Compound 12 in U.S. Pat. No. 7,671,112, Hintzer et al. |
| FC-70 | $N(C_5F_{11})_3$ obtained under the trade designation "3M FLUORINERT ELECTRONIC LIQUID FC-70" | 3M Co. |
| HFPO | Hexafluoropropylene oxide | Chemours Company, Wilmington, DE |

Test Method

Mooney Viscosity Test Method

The Mooney viscosity values were measured in a similar manner as ASTM D 1646-06

Type A by a MV2000 instrument (available from Alpha Technologies, Akron, Ohio) using large rotor (ML 1+10) at 121° C.

Brookfield Viscosity Test Method

The polymer viscosity was measured with a Brookfield viscometer DV-II (available from Brookfield Engineering Laboratories, Inc., Middleboro, Mass., USA) in accordance with ASTM D 2196-05.

Differential Scanning calorimetry (DSC) Test Method

Glass transition temperatures ($T_g$) were determined in accordance with ASTM D 793-01 and ASTM E 1356-98 by a TA Instruments differential scanning calorimetry DSC Q200 (New Castle, Del.) under a nitrogen flow. A DSC thermogram was obtained from the second heat of a heat/cool/heat cycle. The first heat cycle started at −80° C. and was ramped to 300° C. at a 10° C./minute. The cooling cycle started at 300° C. and was cooled to −80° C. at 10° C./min. The second heat cycle started at −80° C. and was ramped to 300° C. at a 10° C./minute.

Example 1: Preparation of a Branched Perfluorinated Ether Acid Fluoride Compound: $(CF_3)_2CFCF(CF_3)OCF(CF_3)C(=O)F$ In a 2 liter (L) PARR reactor (Parr Instrument Company, Moline, Ill.) was first charged with 40 grams (g) (0.7 mole (mol)) spray dried KF sealed and evacuated to 25 millimeter (mm) vacuum. Vacuum charged 1390 g (5.2 mol) $(CF_3)_2CFCOCF_3$ was added along with 174 g of tetraglyme. The reactor was stirred and cooled to 5° C. Addition of 858 g (5.2 mol) HFPO was metered into the reactor over eight hours. The reactor was warmed to 25° C. and the mixture was drained. Column fractionation gave 933 g (2.2 mol) $(CF_3)_2CFCF(CF_3)OCF(CF_3)COF$ having a 102° C. boiling point for a 63% yield based on 66% conversion of the C5 ketone. A second coupling run was run and combined with the first run.

Example 2: Preparation of a Branched Perfluorinated Ether Monomer: MVb5, perfluoro(4,5-dimethyl-2-oxa-1-hexene), $(CF_3)_2CFCF(CF_3)OCF=CF_2$ In a 3-neck 3 L round bottom flask equipped with a mechanical stirrer, condenser, and a thermocouple was charged with 610 g (5.8 mol) of $Na_2CO_3$ and 600 g glyme. The mixture was stirred and heated to 70° C. Over the course of three hours, 2073 g (4.8 mol) $(CF_3)_2CFCF(CF_3)OCF(CF_3)COF$ (from above) was added to the flask and $CO_2$ was produced. After one hour hold, the condenser was changed over for distillation into a receiver and glyme was removed under 50 mm vacuum. Once the glyme was removed, the temperature was set at 105° C. and the flask was isolated. The temperature was raised to 120° C. and the $CO_2$ generated from decarboxylation allowed the vacuum to go to atmospheric pressure. Fluorovinyl ether fluoromonomer was produced and collected in a receiver up to a final reaction temperature of 165° C. Crude product was washed with 300 g deionized (DI) water, followed with 25 g $Na_2CO_3$ in 300 g DI water, and a final wash with 300 g DI water.

Fluorochemical lower phase column fractionation gave 701 g (1.9 mol) $(CF_3)_2CFCF(CF_3)OCF=CF_2$ with a boiling point of 74° C. in 40% yield. FNMR of $CF^aF^b=CF^cOCF^d(CF_3^e)CF^f(CF_3)^g(CF_3)^h$ showed: (a) −121.37 d/d; (b) −114.92 d/d; (c) −134.3 d/d/d; (d) −131.5 m; (e) −77.97 m; (f) −184.6 m; (g) −72.05 m; and (h) −71.85 m.

Comparative Example A: Preparation of a Branched Perfluorinated Ether Monomer: MVb6, perfluoro(4-ethyl-5-methyl-2-oxa-1-hexene), $(CF_3)_2CFCF(CF_2CF_3)OCF=CF_2$ In a 2 L PARR reactor was first charged with 5 g (0.09 mol) spray dried KF, sealed, and evacuated to 25 mm vacuum. Vacuum charged 200 g (0.63 mol) $(CF_3)_2CFCOCF_2CF_3$ was added along with 40 g of tetraglyme. The reactor was stirred and cooled to 5° C. Addition of 107 g (0.65 mol) HFPO was metered into the reactor over 1.5 hours. The reactor was warmed to 25° C. and the mixture was drained. Distillation recovered 197 g of the starting material $(CF_3)_2CFCOCF_2CF_3$ and 2.5 g of coupled acid fluoride boiling from 120-138° C. $(CF_3)_2CFCF(CF_2CF_3)OCF(CF_3)COF$ was identified by FNMR at a 1% yield. No attempt was made to convert the small amount to the fluorinated vinyl ether.

Example 3 (EX-3)

A 4 L reactor was charged with 1,850 g water and was evacuated. This vacuum and pressurization was repeated three times. After removing oxygen, the reactor was heated to 72.2° C. (162° F.). To the reactor was then added 48 g of $CF_3-O-(CF_2)_3-O-CFH-CF_2-COONH_4$ (30% aqueous solution spiked with 1.5% FC-70), 5.2 g ammonium persulfate and 4.26 g ammonium hydroxide. The vacuum was broken and it was pressurized with PMVE (perfluoromethyl vinyl ether) to 0 pounds per square inch (psi) (0 megapascal (MPa)). The reactor was then pressurized to 190 psi (1.3 MPa) with VDF (vinylidene fluoride) and PMVE and with 0.2 ratio. The reactor was agitated at 650 revolutions per minute (rpm). As reactor pressure dropped due to monomer consumption in the polymerization reaction, VDF and PMVE with 0.9 ratio was continuously fed to the reactor to maintain the pressure at 190 psi (1.3 MPa). Pre-emulsified 22% MVb5 with $CF_3-O-(CF_2)_3-O-CFH-CF_2-COONH_4$ (22% aqueous solution) was continuously fed with 0.81 ratio to PMVE feed when 5% (25 grams) of VDF is added. After 126 minutes the monomer feeds were discontinued and the reactor was cooled. The resulting dispersion had a solid content of 34.8 wt. % and a pH of 2.6. The dispersion particle size was 99 nm.

A solution containing 1.25 wt. % $MgCl_2.6H_2O$ in deionized water was used to coagulate the latex. The resulting fluoroelastomer raw gum had a Mooney viscosity of less than 1.0 with ML (1+10) at 121° C. and a Tg of −31.1° C. The fluoropolymer contained 66.9 mol % copolymerized units of VDF, 31.9 mol % PMVE and 1.2 mol % MVb5 by $^1H/^{19}F$-NMR.

The Brookfield viscosity of the polymer at 80° C. was 5870 poise at 1.0 rpm (revolution per minute) using LV4 spindle.

Comparative Example B (CE-B)

Comparative Example B was prepared as Example 3 except that MVb5 was not fed to the reactor. After 84 minutes the monomer feeds were discontinued and the reactor was cooled. The resulting dispersion had a solid content of 33.3 wt. % and a pH of 8.6. The dispersion particle size was 79.4 nm. The resulting fluoroelastomer raw gum had a Mooney viscosity of 120 with ML (1+10) at 121° C. and a Tg of −29.6° C.

Foreseeable modifications and alterations of this invention will be apparent to those skilled in the art without departing from the scope and spirit of this invention. This invention should not be restricted to the embodiments that are set forth in this application for illustrative purposes. To the extent that there is any conflict or discrepancy between this specification as written and the disclosure in any document mentioned or incorporated by reference herein, this specification as written will prevail.

What is claimed is:

1. A fluoropolymer, wherein the fluoropolymer is derived from a composition comprising a vinyl ether compound of the formula $(CF_3)_2CFCF(CF_3)OCF=CF_2$.

2. The fluoropolymer of claim 1, wherein the fluoropolymer is further derived from a polymerizable fluorinated olefinic monomer.

3. The fluoropolymer of claim 2, wherein the polymerizable fluorinated olefinic monomer comprises at least one of tetrafluoroethylene, hexafluoropropylene, vinyl fluoride, vinylidene fluoride, chlorotrifluoroethylene, fluorinated vinyl ether, fluorinated allyl ether, and combinations thereof.

4. The fluoropolymer of claim 1, wherein the fluoropolymer has a viscosity of less than 10,000 poise as measured by a Brookfield viscometer in accordance with ASTM D 2196-05 at 80° C.

5. The fluoropolymer of claim 1, wherein the fluoropolymer is perfluorinated.

6. The fluoropolymer of claim 1, wherein the fluoropolymer is derived from less than 5 mole % of $(CF_3)_2CFCF(CF_3)OCF=CF_2$ versus the total moles of monomers used to derive the fluoropolymer.

7. The fluoropolymer of claim 1, wherein the fluoropolymer is derived from at least 5, mole % $(CF_3)_2CFCF(CF_3)OCF=CF_2$ and at most 60 mole % of $(CF_3)_2CFCF(CF_3)OCF=CF_2$ versus the total moles of monomers used to derive the fluoropolymer.

8. The fluoropolymer of claim 1, wherein the fluoropolymer is derived from at least 40 mole % $(CF_3)_2CFCF(CF_3)OCF=CF_2$ and at most 95 mole % of $(CF_3)_2CFCF(CF_3)OCF=CF_2$ versus the total moles of monomers used to derive the fluoropolymer.

9. The fluoropolymer of claim 1, wherein the fluoropolymer is partially fluorinated.

\* \* \* \* \*